(12) United States Patent (10) Patent No.: US 9,151,741 B2
Forster (45) Date of Patent: Oct. 6, 2015

(54) RFID-BASED DEVICES AND METHODS FOR INITIALIZING A SENSOR

(75) Inventor: Ian James Forster, Essex (GB)

(73) Assignee: Avery Dennison Corporation, Glendale, CA (US)

( * ) Notice: Subject to any disclaimer, the term of this patent is extended or adjusted under 35 U.S.C. 154(b) by 254 days.

(21) Appl. No.: 13/287,243

(22) Filed: Nov. 2, 2011

(65) Prior Publication Data

US 2013/0106396 A1    May 2, 2013

(51) Int. Cl.
*G01N 27/00* (2006.01)
*C40B 70/00* (2006.01)
*G08B 13/14* (2006.01)
*G01N 33/487* (2006.01)

(52) U.S. Cl.
CPC ................................. *G01N 33/48785* (2013.01)

(58) Field of Classification Search
CPC .................................. C40B 70/00; G08B 13/14
USPC ............ 340/10.1, 572.2, 572.1, 572.8, 573.1, 340/573.4, 539.1, 539.17, 568.1, 10.51; 600/310; 210/435; 320/108; 324/71.1, 324/629; 422/186–187; 204/155–158
See application file for complete search history.

(56) References Cited

U.S. PATENT DOCUMENTS

| 7,557,708 | B1 | 7/2009 | Pacholok et al. | |
| 7,605,706 | B2 * | 10/2009 | Khatri | 340/572.7 |
| 7,653,919 | B2 | 1/2010 | Potyrailo et al. | |
| 7,688,182 | B2 | 3/2010 | Nagai | |
| 8,306,592 | B2 * | 11/2012 | Takizawa et al. | 600/310 |
| 2005/0218066 | A1 * | 10/2005 | Keane | 210/435 |
| 2007/0090927 | A1 | 4/2007 | Potyrailo et al. | |
| 2007/0114621 | A1 | 5/2007 | Wisnudel et al. | |
| 2008/0135614 | A1 * | 6/2008 | Werner et al. | 235/439 |
| 2009/0033294 | A1 * | 2/2009 | Odajima et al. | 320/166 |
| 2009/0146810 | A1 * | 6/2009 | Monk et al. | 340/572.1 |
| 2009/0218891 | A1 | 9/2009 | McCollough, Jr. | |
| 2009/0256679 | A1 * | 10/2009 | Potyrailo et al. | 340/10.1 |
| 2010/0060456 | A1 * | 3/2010 | Forster | 340/572.7 |
| 2010/0134286 | A1 * | 6/2010 | Potyrailo et al. | 340/572.1 |
| 2012/0126745 | A1 * | 5/2012 | Partovi et al. | 320/108 |
| 2012/0153968 | A1 * | 6/2012 | Forster | 324/629 |

FOREIGN PATENT DOCUMENTS

| FR | WO2012/002808 | * | 6/2010 | ............ G01N 21/21 |
| GB | 2425691 | | 11/2006 | |

* cited by examiner

*Primary Examiner* — Arleen M Vazquez
*Assistant Examiner* — Neel Shah
(74) *Attorney, Agent, or Firm* — Avery Dennison Corporation

(57) ABSTRACT

An RFID-based analyte sensor is provided with an antenna adapted to receive energy from an RF field and produce a signal. A sensing material is electrically connected to the antenna and has an electrical property which varies in the presence of an analyte. An energy storage device is also electrically connected to the antenna and is adapted to receive and store energy from the antenna and selectively discharge the stored energy. An initializing element is electrically connected to the energy storage device and is energized by the stored energy discharged by the energy storage device. When the initializing element is energized, it operates to reduce the analyte content of at least a portion of the sensing material, effectively initializing the sensing material.

19 Claims, 1 Drawing Sheet

RFID-BASED DEVICES AND METHODS FOR INITIALIZING A SENSOR

FIELD OF THE DISCLOSURE

The present subject matter relates to radio frequency identification ("RFID") devices. More particularly, the present subject matter relates to sensor devices incorporating RFID technology.

DESCRIPTION OF RELATED ART

Electrically powered devices for analyte sensing are well known. Recently, analyte sensors incorporating RFID technology have been proposed as a means for providing a sensing function at a relatively low power requirement. Exemplary analyte sensors incorporating RFID technology are described in U.S. Patent Application Publication No. 2008/0135614 to Werner et al., which is incorporated herein by reference. Such devices typically include an analyte-sensitive material and an antenna electrically connected to each other. When the antenna is energized, it sends a signal to a receiver device or controller which analyzes the signal. One or more of the electrical properties of the sensing material (typically its resistance) change when in the presence of the analyte, which modifies the signal being transmitted by the antenna. The controller is programmed to analyze the modified signal and produce an output indicative of the presence of the analyte in the vicinity of the sensing material and/or one or more properties of the analyte (e.g., its concentration in a substance).

One disadvantage of known RFID-based analyte sensors is that the sensing material can become saturated by an analyte, such as a solvent or other materials. When the sensing material has become saturated, the accuracy of readings taken by the sensor degrades. Accordingly, it would be advantageous to provide an RFID-based analyte sensor capable of initializing or refreshing sensing material which has become saturated.

SUMMARY OF THE INVENTION

There are several aspects of the present subject matter which may be embodied separately or together in the devices and systems described and claimed below. These aspects may be employed alone or in combination with other aspects of the subject matter described herein, and the description of these aspects together is not intended to preclude the use of these aspects separately or the claiming of such aspects separately or in different combinations as set forth in the claims appended hereto.

In one aspect, an RFID-based analyte sensor includes an antenna adapted to receive energy from an RF field and produce a signal. A sensing material is electrically connected to the antenna and has an electrical property which varies in the presence of an analyte. An energy storage device is also electrically connected to the antenna and is adapted to receive and store energy from the antenna and selectively discharge the stored energy. An initializing element is electrically connected to the energy storage device and is energized by the stored energy discharged by the energy storage device. When the initializing element is energized, it operates to reduce the analyte content of at least a portion of the sensing material.

In another aspect, a method for reducing the analyte content of a portion of an RFD-based analyte sensor comprises providing energy to the analyte sensor. At least a portion of the energy is stored and then selectively discharged to energize an initializing element. The initializing element is operated to treat a portion of the analyte sensor, thereby reducing the analyte content thereof.

In a still further aspect of the present invention, the analyte material is directly connected to the chip through one or more sensing ports. The condition of the sensor will then affect some parameter of the communication from the chip, such as frequency or phase of a sub carrier, or alternatively, the condition of the sensor material can alter a digital value which can be transferred as part of a data communication sequence between the reader and the tag.

DETAILED DESCRIPTION OF THE EMBODIMENTS

As required, detailed embodiments of the present invention are disclosed herein; however, it is to be understood that the disclosed embodiments are merely exemplary of the invention, which may be embodied in various forms. Therefore, specific details disclosed herein are not to be interpreted as limiting, but merely as a basis for the claims and as a representative basis for teaching one skilled in the art to variously employ the present invention in virtually any appropriate manner.

Figure 2:
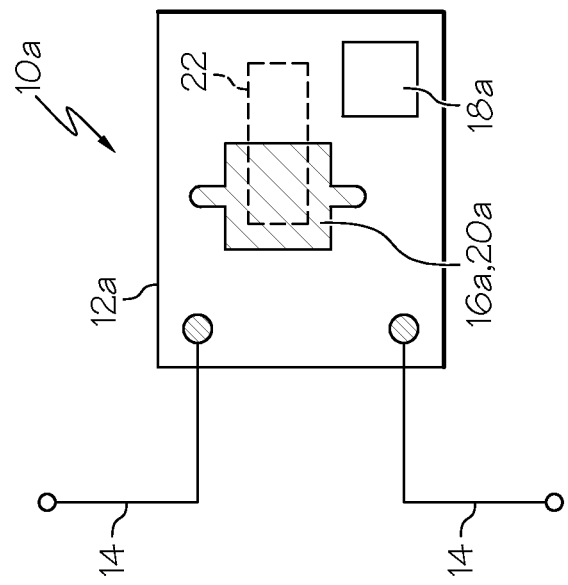
FIG. 2 is a schematic diagram of an RFID-based analyte sensor having an energy storage device and initializing element which are integrated in a chip.
Figure 1:
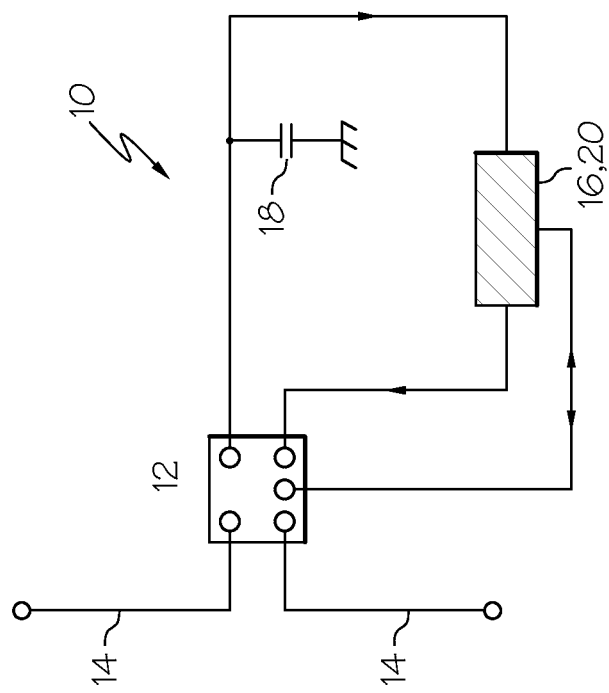
FIG. 1 is a schematic diagram of an RFID-based analyte sensor having an external energy storage device and initializing element.

According to the methods and devices described herein, an analyte-saturated portion of an RFID-based analyte sensor is refreshed or initialized by an initializing element which performs such function upon receiving stored energy from an energy storage device. FIGS. 1 and 2 illustrate two embodiments of RFID-based analyte sensors 10 and 10a incorporating aspects of the present invention.

In the embodiment of FIG. 1, the RFID-based analyte sensor 10 comprises an RF communication chip 12, which may include an integrated circuit for controlling RF communication and other functions of the analyte sensor 10. The RF communication chip 12 is electrically connected or coupled to an antenna 14 which is adapted to receive energy from an RF field and produce a signal which is transmitted to one or more external devices, such as a controller or reader or detector, which receives and analyzes the signal. The RF field may be generated by the device to which the antenna 14 transmits the signal or it may be generated by a different external device. The antenna 14 may be any of a variety of antenna types, such as a dipole antenna, loop antenna, slot antenna, or a hybrid combining characteristics of these antenna types.

The RF communication chip 12 is electrically connected or coupled to an analyte-sensitive material 16. The sensing material may be integrated in the chip (FIG. 2, designated as 16a) or provided externally of the chip 12 (FIG. 1, designated as 16). The sensing material 16, 16a has an electrical property which varies in the presence of an analyte, such that the signal produced by the antenna 14 will change when an analyte comes into contact with the sensing material. If the signal transmitted by the antenna 14 is the same before and after the sensing material 16, 16a is placed in the vicinity of a substance, it is indicative that the substance does not contain any of the target analyte. On the other hand, if the RFID reader detects a difference between the signals, it is indicative that the substance contains an amount of the target analyte. In one embodiment, the sensing material is an interdigital structure loaded with a dielectric material which causes the resistance of the sensing material (and, hence, the signal transmitted by the antenna 14) to change in the presence of an analyte. Other sensing materials may also be employed without departing from the scope of the present disclosure.

The RF communication chip is also electrically connected or coupled to an energy storage device (18 in FIGS. 1 and 18a in FIG. 2). The energy storage device 18 receives energy from the antenna 14 and stores the energy for later use to power an initializing element 20, 20a upon the occurrence of a predetermined stimulus, as will be described in greater detail herein. The energy storage device may be any of a variety of types of devices. In the illustrated embodiment, the energy storage device 18, 18a is of the type which stores energy as differential electrostatic charge, namely a capacitor. However, other energy storage devices (e.g., one of the type which stores energy as chemical potential, such as a battery) may also be employed without departing from the scope of the present disclosure.

Alternatively, the analyte material can be connected directly to the chip through one or more sensing ports on the chip. The condition of the sensor will then affect some parameter of the communication from the chip, such as frequency or phase of a sub carrier, or alternatively, the condition of the sensor material can alter a digital value which can be transferred as part of a data communication sequence between the reader and the tag.

The energy storage device 18, 18a is electrically connected or coupled to the initializing element (20 in FIGS. 1 and 20a in FIG. 2). In the embodiment of FIG. 1, the sensing material 16, 16a and initializing element are integrated into a single component, for example, in the form of a resistive material which is coated with a substance which causes the resistance of the resistive material to change in the presence of an analyte. Alternatively, the sensing material and the initializing element may be separately provided.

The initializing element 20, 20a is not directly energized (or, as in the illustrated embodiment, is not energized to the extent necessary to perform an initialization function) by energy from the antenna 14. Instead, the initializing element performs its initialization function upon receipt of the stored energy discharged by the energy storage device 18, 18a. When the initializing element becomes sufficiently energized by the energy storage device, it operates to reduce the analyte content of at least a portion of the analyte sensor 10, 10a. Most advantageously, the initializing element is positioned and configured to reduce or eliminate the analyte content of at least a portion of the sensing material 16, 16a. The initializing element and the sensing material may be collocated, for example, with them being positioned in a generally vertical stack or positioned adjacent to each other in the same plane or layer.

Close positioning of the initializing element 20, 20a and the sensing material 16, 16a may be advantageous if the initializing element is provided as a heater configured to raise the temperature of at least a portion of the sensing material. Using the embodiment of FIG. 1 as an example, the temperature of the initializing element 20 may be increased by passing a relatively high current through it. When the initializing element 20 and, hence, the sensing material 16 reach a certain temperature (which may vary according to the nature of the sensing material 16, the substance to be analyzed, and the target analyte), at least a portion of the analyte will have evaporated from the sensing material 16. Typically, the sensing material 16 is heated until substantially all of the analyte will have been removed from it, effectively refreshing or initializing the sensing material 16.

Other types of initializing elements allow for different positioning with regard to the associated sensing material 16, 16a. For example, the initializing element 20, 20a may be provided as a light generator which is configured to treat the sensing material with light energy to reduce or eliminate analyte therefrom. In this case, the initializing element need not be directly adjacent to the sensing material, but is advantageously positioned so as to direct light energy thereto. Alternatively, the initializing element 20, 20a may be provided as an electric field generator which is configured to generate an electric field in the vicinity of the sensing material 16 to reduce or eliminate analyte therefrom. In that case, it may be advantageous for the initializing element to be generally adjacent to the sensing material 16, 16a to minimize the magnitude of the electric field needed to be generated to reduce the analyte content of the sensing material and the effect of the electric field on other components of the analyte sensor 10, 10a and the surrounding environment. In yet another alternative embodiment, the initializing element may be provided as an ultrasound generator which is configured to treat the sensing material with ultrasonic energy to reduce or eliminate analyte therefrom. In that case, the initializing element 20 need not be directly adjacent to the sensing material 16, but is advantageously positioned so as to direct ultrasonic energy thereto.

The period over which the initializing element 20, 20a provides the initialization function may vary without departing from the scope of the present disclosure. For example, in one embodiment, the energy storage device 18, 18a may be configured to discharge its stored energy to the initializing element for a predetermined amount of time. In another embodiment, the energy storage device may be configured to discharge all of its stored energy to the initializing element. In yet another embodiment, the energy storage device is configured to discharge its stored energy to the initializing element until a characteristic of the initializing element and/or the sensing material 16, 16a is equal to a predetermined value. For example, if the initializing element is provided as a heater, the energy storage device may be configured to discharge its stored energy to the heater until the temperature of the heater and/or the sensing material 16 (as detected by a secondary sensor) reaches a predetermined value.

Regardless of the nature of the initializing element 20, 20a, the analyte sensor 10, 10a may also include an initialization sensor which measures the effect of the initializing element on the sensing material 16, 16a. For example, when the initializing element is provided as a heater, the initialization sensor can measure the temperature of the initializing element and/or the sensing material 16, 16a and transmit such information to the controller or reader or detector, which compares the temperature to the signal being transmitted by the antenna 14. By taking multiple readings at different temperatures, the effect of temperature on the analyte can be determined, which in turn may be used to determine other characteristics of the analyte (e.g., its boiling point). The same is true for other types of initializing elements, for example, an initialization sensor may be employed in combination with an initializing element 20, 20a provided as an electric field generator to determine the effect of electricity on the analyte, which may be used to determine various characteristics of the analyte.

The analyte sensor 10a of FIG. 2 differs principally from the analyte sensor 10 of FIG. 1 in that the energy storage device 18a and the initializing element 20a are integrated in the chip 12a in FIG. 2, but provided externally of the chip 12 in FIG. 1. As in FIG. 1, the sensing material 16a and the initializing element 20a of FIG. 2 are integrated into a single component, for example, in the form of a resistive pad which is coated with a substance which causes the resistance of the resistive pad to change in the presence of an analyte. Alternatively, the sensing material 16a and the initializing element 20a may be separately provided.

A contact element 22 is associated with the illustrated resistive pad to receive stored energy discharged from the energy storage device 18a. In the illustrated embodiment, the energy storage device 18a is a capacitor and the contact element 22 is a capacitive top contact.

In one exemplary method of using the analyte sensor 10, 10a, the RF field transmits energy to the antenna 14, which is passed through the chip 12, 12a to the energy storage device 18, 18a and the sensing material 16, 16a for an analyte-sensing procedure. A portion of the energy rectified by the antenna 14 is stored in the energy storage device.

During the analyte-sensing procedure, a substance comes into contact with the sensing material 16, 16a. The times and manner in which measurements are taken may depend upon a variety of factors. In one embodiment, the analyte sensor 10, 10a may remain in the field of view of the RFID reader, with measurements being taken periodically. In another embodiment, which may be employed with sensing material which adsorbs the analyte over time, the analyte sensor may leave the field of view of the RFID reader. After a time, the analyte sensor is then brought back into the field of view of the RFID reader and read to determine the presence of analyte, with the value measured by the RFID reader being indicative of the integrated exposure of the sensing material to the analyte over the intervening time.

If the substance is free of the analyte, the electrical properties of the sensing material 16, 16a will remain constant, which causes the signal transmitted by the antenna 14 to remain constant. The controller or reader or detector analyzes the signal and, seeing that it is constant, produces an output which indicates that the analyte is not present in the substance. On the other hand, if the substance contains an amount of the analyte, at least one electrical property of the sensing material 16, 16a (for example, the resistance) changes, which modifies the signal transmitted by the antenna 14. The controller analyzes the signal and, seeing that it has changed from a baseline signal, produces an output indicative of the presence of the analyte and/or one or more properties of the analyte (for example, its concentration in the substance). FIG. 1 provides that the sensing material 16, 16a is connected to the chip 12 to one or more sensing ports on the chip.

At some point, which may occur after the analyte-sensing procedure is complete or during the procedure or between consecutive steps of the procedure, a predetermined stimulus is applied to the energy storage device 18, 18a. The antenna 14 may or may not be receiving energy from an RF field at the time the predetermined stimulus is applied. Upon receiving the stimulus, the energy storage device 18 discharges some or all of its stored energy to the initializing element 20, 20a, which energizes the initializing element to the point that the initializing element functions to reduce the analyte content of the sensing material 16, 16a (as described previously).

The predetermined stimulus that triggers the energy storage device 18, 18a to discharge the stored energy may be any of a wide variety of events. For example, the stimulus may be a particular signal from the RF field, such as a signal at a different frequency than the one typically transmitted to energize the analyte sensor 10, 10a. In another embodiment, the absence of a signal from the RF field may be used as a stimulus. In yet another embodiment, the stimulus may be the energy storage device 18, 18a reaching a certain level of stored energy. Other stimuli may also be employed without departing from the scope of the present disclosure.

Once the initializing element 20, 20a is energized to the proper level, it will function to reduce the amount of analyte adsorbed by the sensing material 16, 16a and/or adjacent thereto. For example, if the initializing element is a heater its temperature will rise, which increases the temperature of the surrounding region of the analyte sensor 10, 10a, particularly the sensing material 16, 16a. Any analyte or other foreign substance remaining on or around the sensing material will evaporate, thereby refreshing or initializing the sensing material in preparation for another analyte-sensing procedure. The initializing function may be provided continuously as long as the energy storage device 18, 18a is able to provide power or, alternatively, the energy storage device may provide pulsed power to the initializing element for intermittent operation. In yet another embodiment, the energy storage device may initially provide continuous power to the initializing element upon occurrence of the stimulus and may subsequently shift to pulsed power discharge upon the occurrence of another event (for example, when the amount of energy remaining in the energy storage device falls below a certain level of the energy storage capacity of the energy storage device).

Variations may be made to the analyte sensors and methods disclosed herein without departing from the scope of the present disclosure, such as an embodiment wherein the chip itself may provide an initializing function. For example, in an embodiment wherein initialization of sensing material is achieved by raising its temperature, the chip itself may serve as the heater or initializing element. The stored energy from the energy storage device is dissipated into the chip itself, which raises its temperature and has the effect of evaporating any analyte in the surrounding area. In such an embodiment, an analyte-sensitive substance may be coated on the chip, allowing it to perform the functions of both the sensing material and the initializing element.

It will be understood that the embodiments described above are illustrative of some of the applications of the principles of the present subject matter. Numerous modifications may be made by those skilled in the art without departing from the spirit and scope of the claimed subject matter, including those combinations of features that are individually disclosed or claimed herein. For these reasons, the scope hereof is not limited to the above description but is as set forth in the following claims, and it is understood that claims may be directed to the features hereof including as combinations of features that are individually disclosed or claimed herein.

What is claimed:

1. An RFID-based analyte sensor, comprising:
   an antenna adapted to receive energy from an RF field and produce a signal;
   a sensing material electrically connected to the antenna and having an electrical property which varies in the presence of an analyte;
   an energy storage device electrically connected to the antenna and adapted to receive and store energy from the antenna and selectively discharge the stored energy;
   an initializing element electrically connected to the energy storage device and energized by the stored energy discharged by the energy storage device, wherein the initializing element operates to reduce the analyte content of at least a portion of the sensing material and the energy storage device, the initialing element and the sensing material are integrated in a RFID chip;

a RFID reader for receiving the signal produced by the antenna, wherein the signal produced by the antenna is based at least in part on said electrical property of the sensing material, and the RFID reader is programmed to compare the effect of the initializing element to the signal produced by the antenna to determine a characteristic of an analyte.

2. The sensor of claim 1, wherein the initializing element comprises a heater configured to raise the temperature of said at least a portion of the sensing material to a sufficient level to reduce the analyte content thereof.

3. The sensor of claim 1, wherein the initializing element comprises a light generator configured to treat said at least a portion of the sensing material with light energy to reduce the analyte content thereof.

4. The sensor of claim 1, wherein the initializing element comprises an electric field generator configured to generate an electric field in the vicinity of said at least a portion of the sensing material to reduce the analyte content thereof.

5. The sensor of claim 1, wherein the initializing element comprises an ultrasound generator configured to treat said at least a portion of the sensing material with ultrasonic energy to reduce the analyte content thereof.

6. The sensor of claim 1, wherein the energy storage device comprises a capacitor.

7. The sensor of claim 1, further comprising an initialization sensor for measuring the effect of the initializing element on said at least a portion of the sensing material.

8. The sensor of claim 1, wherein the energy storage device is configured to stop discharging the stored energy after a predetermined time.

9. The sensor of claim 1, wherein the energy storage device is configured to discharge all of the stored energy.

10. The sensor of claim 1, wherein the energy storage device is configured to stop discharging the stored energy when a characteristic of the initializing element and/or the sensing material is equal to a predetermined value.

11. A method for reducing the analyte content of a portion of an RFID-based analyte sensor, comprising:

providing energy to the analyte sensor from a RFID chip;
storing at least a portion of the energy;
selectively discharging the stored energy to energize an initializing element;
operating the initializing element to treat a portion of the analyte sensor, thereby reducing the analyte content thereof wherein the sensor includes a RFID reader for receiving the signal produced by the antenna, wherein the signal produced by the antenna is based at least in part on said electrical property of the sensing material, and comparing the effect of the initializing element to the signal produced by the antenna via the RFID reader to determine a characteristic of an analyte.

12. The method of claim 11, wherein said selectively discharging the stored energy includes raising the temperature of said portion of the analyte sensor.

13. The method of claim 11, wherein said selectively discharging the stored energy includes treating said portion of the analyte sensor with light energy.

14. The method of claim 11, wherein said selectively discharging the stored energy includes generating an electric field in the vicinity of said portion of the analyte sensor.

15. The method of claim 11, wherein said selectively discharging the stored energy includes treating said portion of the analyte sensor with ultrasonic energy.

16. The method of claim 11, further comprising measuring the effect of the initializing element on said portion of the analyte sensor.

17. The method of claim 16, further comprising producing a signal from the analyte sensor and comparing the signal to the effect of the initializing element on said portion of the analyte sensor to determine a characteristic of an analyte.

18. An RFID-based analyte sensor, comprising:

an antenna adapted to receive energy from an RF field and produce a signal;
a sensing material electrically integrated within a chip;
an energy storage device electrically connected to the antenna and adapted to receive and store energy from the antenna and selectively discharge the stored energy;
an initializing element electrically connected to the energy storage device and energized by the stored energy discharged by the energy storage device;
a RFID reader for receiving the signal produced by the antenna, wherein the signal produced by the antenna is based at least in part on said electrical property of the sensing material, and the RFID reader is programmed to compare the effect of the initializing element to the signal produced by the antenna to determine a characteristic of an analyte; and
wherein a condition of the sensing material alters a parameter or digital value of communication from the chip.

19. The RFID-based analyte sensor of claim 18 wherein the parameter is one of frequency or phase of a sub-carrier.

* * * * *